(12) United States Patent
Holakovsky et al.

(10) Patent No.: US 8,650,840 B2
(45) Date of Patent: Feb. 18, 2014

(54) RESERVOIR FOR NEBULIZER WITH A DEFORMABLE FLUID CHAMBER

(75) Inventors: Holger Holakovsky, Ingelheim am Rhein (DE); Matthias Hausmann, Ingelheim am Rhein (DE); Guido Schmiedel, Ingelheim am Rhein (DE); Florian Witte, Ingelheim am Rhein (DE); Johannes Geser, Ingelheim am Rhein (DE); Gerald Mathe, Ingelheim am Rhein (DE); Martin Meisenheimer, Ingelheim an Rhein (DE); Antonino Lanci, Bern (CH); Elmar Mock, Colombier (CH); Martin Sigrist, Aarberg (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 876 days.

(21) Appl. No.: 12/405,361

(22) Filed: Mar. 17, 2009

(65) Prior Publication Data

US 2009/0235924 A1    Sep. 24, 2009

(30) Foreign Application Priority Data

Mar. 17, 2008   (DE) .......................... 10 2008 014 464

(51) Int. Cl.
| | |
|---|---|
| *B65B 3/16* | (2006.01) |
| *B65D 83/00* | (2006.01) |
| *B65B 7/14* | (2006.01) |
| *A61M 11/00* | (2006.01) |
| *B05B 11/04* | (2006.01) |
| *B65B 31/00* | (2006.01) |

(52) U.S. Cl.
USPC .................... 53/434; 53/440; 53/469; 53/486

(58) Field of Classification Search
CPC ............ B67C 3/223; B65B 7/14; B65B 3/16; B65B 3/18; B65B 3/003; B65B 3/045; B65B 61/24; B05B 11/0054; B05B 11/0043; B65D 83/62; B65D 83/42; B65D 83/0055; A61M 11/00
USPC ............ 53/433, 434, 440, 469, 470, 486, 289
IPC ..................... B65B 7/06, 7/14, 61/24
See application file for complete search history.

(56) References Cited

U.S. PATENT DOCUMENTS 1,828,864 A * 10/1931 Hopkins ......................... 53/469
2,127,401 A *  8/1938 Gillican ......................... 53/469

(Continued)

FOREIGN PATENT DOCUMENTS

| CN | 1125426 A | 6/1996 |
|---|---|---|
| CN | 1849174 A | 10/2006 |

(Continued)

OTHER PUBLICATIONS

International Search Report for International Application No. PCT/EP2009/001619 dated Oct. 6, 2009, 1 page.

*Primary Examiner* — Stephen F Gerrity
(74) *Attorney, Agent, or Firm* — Roberts Mlotkowski; Safran & Cole, P.C.; David S. Safran

(57) ABSTRACT

A reservoir for a nebulizer, a nebulizer and a method of filling a reservoir are proposed. To avoid undesirable rises in pressure, a fluid chamber of the reservoir is pre-collapsed and filled with an initial amount of fluid which is less than the maximum volume of the fluid chamber. Preferably, before being filled, the fluid chamber is compressed and/or expanded by means of gas to a defined volume which is less than the maximum volume of the fluid chamber.

20 Claims, 6 Drawing Sheets

(56) References Cited

U.S. PATENT DOCUMENTS

Figure 1:
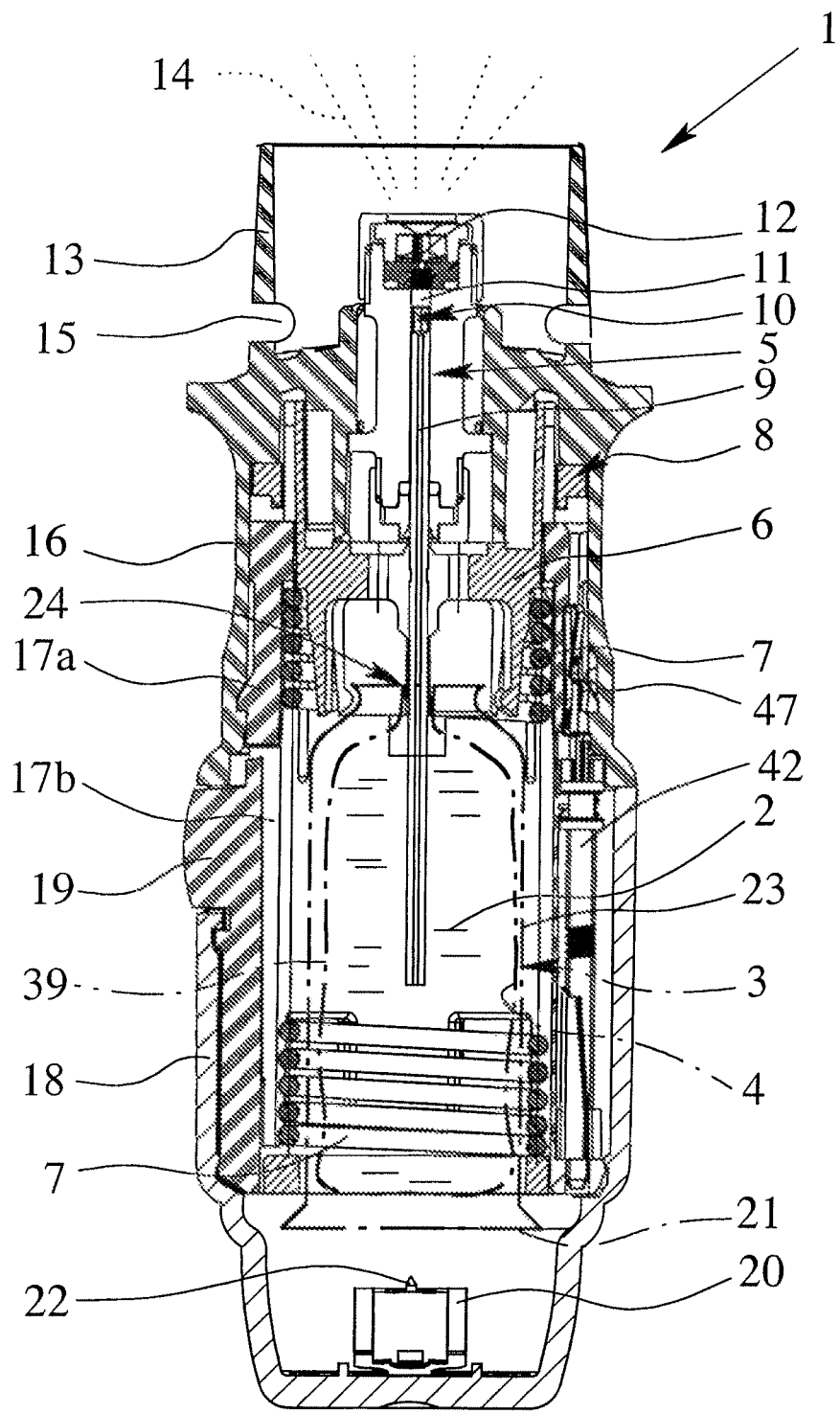

| | | | | |
|---|---|---|---|---|
| 2,161,071 | A * | 6/1939 | McGrath et al. | 53/434 |
| 2,329,311 | A * | 9/1943 | Waters | 53/289 |
| 3,196,587 | A * | 7/1965 | Hayward et al. | 53/440 |
| 3,299,603 | A * | 1/1967 | Shaw | 53/469 |
| 3,457,694 | A * | 7/1969 | Tatibana | 53/289 |
| 3,491,803 | A * | 1/1970 | Galik | 53/289 |
| 3,590,557 | A * | 7/1971 | Vogel | 53/289 |
| 3,674,060 | A * | 7/1972 | Ruekberg | 53/289 |
| 3,973,603 | A * | 8/1976 | Franz | 53/289 |
| 4,338,765 | A * | 7/1982 | Ohmori et al. | 53/289 |
| 4,840,017 | A * | 6/1989 | Miller et al. | 53/469 |
| 4,905,450 | A * | 3/1990 | Hansen et al. | 53/469 |
| 4,926,613 | A * | 5/1990 | Hansen | 53/433 |
| 5,014,492 | A * | 5/1991 | Fiorini et al. | 53/434 |
| 5,237,797 | A * | 8/1993 | Varlet | 53/469 |
| 5,261,565 | A | 11/1993 | Drobish et al. | |
| 5,271,153 | A | 12/1993 | Reiboldt et al. | |
| 5,282,304 | A | 2/1994 | Reiboldt et al. | |
| 5,499,750 | A | 3/1996 | Manifold | |
| 5,833,088 | A | 11/1998 | Kladders et al. | |
| 5,950,403 | A * | 9/1999 | Yamaguchi et al. | 53/469 |
| 6,062,430 | A | 5/2000 | Fuchs | |
| 6,223,933 | B1 | 5/2001 | Hochrainer et al. | |
| 6,375,048 | B1 | 4/2002 | van der Meer et al. | |
| 6,405,872 | B1 * | 6/2002 | Ruther et al. | 53/434 |
| 6,685,691 | B1 | 2/2004 | Freund et al. | |
| 6,825,441 | B2 | 11/2004 | Katooka et al. | |
| 6,942,127 | B2 | 9/2005 | Raats | |
| 6,988,496 | B1 | 1/2006 | Eicher et al. | |
| 7,090,093 | B2 | 8/2006 | Hochrainer et al. | |
| 7,380,575 | B2 * | 6/2008 | Stricklin | 53/469 |
| 7,802,568 | B2 | 9/2010 | Eicher et al. | |
| 2002/0007155 | A1 | 1/2002 | Freund et al. | |
| 2003/0039915 | A1 * | 2/2003 | Holt et al. | 53/440 |
| 2003/0064032 | A1 | 4/2003 | Lamche et al. | |
| 2003/0085254 | A1 | 5/2003 | Katooka et al. | |
| 2004/0139700 | A1 * | 7/2004 | Powell et al. | 53/469 |
| 2004/0143235 | A1 | 7/2004 | Freund et al. | |
| 2005/0269359 | A1 | 12/2005 | Raats | |
| 2006/0016449 | A1 | 1/2006 | Eicher et al. | |
| 2006/0239930 | A1 | 10/2006 | Lamche et al. | |
| 2011/0239594 | A1 * | 10/2011 | Nottingham et al. | 53/469 |

FOREIGN PATENT DOCUMENTS

| | | |
|---|---|---|
| CN | 1299662 C | 2/2007 |
| DE | 20 2006 017 793 U1 | 2/2007 |
| EP | 0 386 800 A1 | 9/2009 |
| ES | 2 228 479 T3 | 4/2005 |
| ES | 2 262 348 T3 | 11/2006 |
| JP | 56-084246 A | 7/1981 |
| JP | 09-002442 A | 1/1997 |
| JP | 09-077073 A | 3/1997 |
| JP | 2002-532216 A | 10/2002 |
| JP | 2007-534379 A | 11/2007 |
| WO | 86/05419 A1 | 9/1986 |
| WO | 89/00889 A1 | 2/1989 |
| WO | 89/00947 A1 | 2/1989 |
| WO | 93/25321 A1 | 12/1993 |
| WO | 94/25371 A1 | 11/1994 |
| WO | 99/11563 A1 | 3/1999 |
| WO | 00/27543 A1 | 5/2000 |
| WO | 00/37336 A1 | 6/2000 |
| WO | 00/49988 A2 | 8/2000 |
| WO | 01/87392 A2 | 11/2001 |
| WO | 01/97888 A2 | 12/2001 |
| WO | 01/98175 A1 | 12/2001 |
| WO | 01/98176 A2 | 12/2001 |
| WO | 03/014832 A1 | 2/2003 |
| WO | 03/050031 A1 | 6/2003 |
| WO | 2004/033954 A2 | 4/2004 |
| WO | 2005/014175 A1 | 2/2005 |
| WO | 2005/109948 A2 | 11/2005 |
| WO | 2006/011638 A1 | 2/2006 |
| WO | 2006/125577 A2 | 11/2006 |
| WO | 2007/011475 A1 | 1/2007 |

* cited by examiner

RESERVOIR FOR NEBULIZER WITH A DEFORMABLE FLUID CHAMBER

BACKGROUND OF THE INVENTION

1. Field of Invention

The present invention relates to a reservoir, particularly for a nebulizer, having a preferably deformable fluid chamber containing a fluid, a nebulizer with such a reservoir and to a method of filling such a reservoir with fluid.

2. Description of Related Art

From International Patent Application Publication Nos. WO 96/06011 (corresponding to U.S. Pat. No. 5,833,088) A1 and WO 00/49988 A2 and WO 99/43571 A1, a reservoir or container for a nebulizer or inhaler is known. The container has a rigid casing and a bag contained therein. The bag contains a medicament preparation and collapses when the medicament preparation is removed. Hitherto, efforts have been made to fill the bag substantially completely with the medicament liquid, in particular, in order to displace any gas contained therein. However, in practice, this is not carried out totally free from residual gas or gas bubbles. During storage of the container, a substantial pressure can build up in the bag containing the medicament preparation. When the container is opened for the first time, particularly by piercing, this may lead to an undesirable escape or loss of the medicament preparation.

For example, if an ethanolic medicament preparation is used, a partial air pressure prevails in the fluid chamber which is usually substantially lower than ambient pressure. This partial pressure difference makes it possible for air to diffuse slowly into the bag. This may lead to an unwanted increase in the pressure in the bag. The vapor pressure of ethanol, which varies considerably depending on the temperature, may also lead to unwanted increases or variations in pressure. In addition, a pressure increase may occur as a result of the temperature-induced expansion of the liquid in the fluid chamber.

SUMMARY OF THE INVENTION

The aim of the present invention is to provide a reservoir containing a fluid, particularly a medicament preparation, a nebulizer having a reservoir and a method of filling a reservoir with a fluid, in which an undesirable rise in the pressure acting on the fluid in a fluid chamber can be prevented or at least minimized.

The above aim is achieved by means of a reservoir, a nebulizer and a method as described herein.

According to a first aspect of the present invention, the fluid chamber being filled with the fluid has been deformed, folded, creased, rolled, at least partially compressed and/or pre-collapsed. Alternatively or additionally, the maximum volume of the fluid chamber is greater than the (initial or maximum) fill quantity of fluid. Thanks to this "under-filling," an undesirable rise in the pressure in the fluid chamber, even, in particular, when the still sealed reservoir is stored for long periods, can be prevented by a simple but effective method.

According to another aspect of the present invention, the fluid chamber is filled with the fluid or sealed under reduced pressure and/or before being filled is expanded to a defined volume which is preferably less than the maximum volume of the fluid chamber. Alternatively or additionally, the fluid chamber is pre-collapsed during or before the filling with the fluid to a volume which is less than the maximum volume, and/or placed under pressure externally and/or restricted in its spatial expansion. In this way, too, under-filling of the fluid chamber can be achieved and an undesirable rise in the pressure in the fluid chamber, even when the still sealed reservoir is stored for long periods, can be prevented or at least minimized.

According to another aspect of the present invention, the fluid chamber is filled under a protective gas atmosphere, e.g., carbon dioxide, helium or the like. If necessary, a corresponding gas bubble can be formed in the fluid chamber. Preferably, the protective gas then subsequently diffuses slowly out of the fluid chamber and/or is reabsorbed or dissolved by the fluid, for example carbon dioxide in an aqueous fluid, in particular. Accordingly, a gas bubble may be formed with vapor, particularly consisting of the vapor of a solvent of the fluid, during filling.

According to another aspect of the present invention, the fluid chamber is filled with the fluid in a manner that is at least substantially free from residual gas and/or gas bubbles. The avoidance of residual gas or gas bubbles in conjunction with the under-filling or incomplete filling of the preferably flexible, deformable and/or collapsible fluid chamber leads to a particularly safe and effective avoidance of the build-up of an undesirable pressure in the fluid chamber, even during lengthy storage of the still sealed reservoir and/or under highly variable ambient conditions (temperature, humidity, pressure or the like).

According to another aspect it is also possible to fill the container with fluid at elevated temperature, i.e., to transfer heated fluid, in particular, into the fluid chamber. Preferably the fluid is only cooled (or cools down automatically) after the fluid chamber or reservoir has been sealed, as a result of which the desired pre-collapsing or under-filling can be at least partly completed and/or carried out free from gas bubbles.

In another aspect of the present invention, the fluid chamber is initially filled to the maximum level. This enables the fluid chamber to be expanded in particular to the maximum as well, so that pre-expansion can be dispensed with. Then, some of the fluid added can be removed again, particularly by suction, to achieve only partial filling or under-filling.

The features and aspects of the present invention described above and the other features and aspects of the present invention may be implemented independently of one another or in any desired combination.

Further advantages, features, properties and aspects of the present invention will become apparent from the following description of preferred embodiments with reference to the accompanying drawings.

BRIEF DESCRIPTION OF THE DRAWINGS

FIG. 1 is a schematic section through a proposed nebulizer in the relaxed state;

FIG. 2 is a schematic section through the nebulizer, rotated through 90° compared with FIG. 1, in the tensioned state with a reservoir according to a first embodiment;

FIG. 3 is a view of a reservoir according to a second embodiment;

FIG. 4 is the reservoir of FIG. 3 with the device expanded for pre-collapsing;

FIG. 5 is a schematic section through the reservoir in FIG. 3; and

FIG. 6 is a schematic section through a proposed reservoir according to a third embodiment.

DETAILED DESCRIPTION OF THE INVENTION

In the figures, the same reference numerals have been used for identical or similar components, where, in particular, corresponding or comparable properties and advantages are obtained even through the associated description is not repeated.

Figure 2:
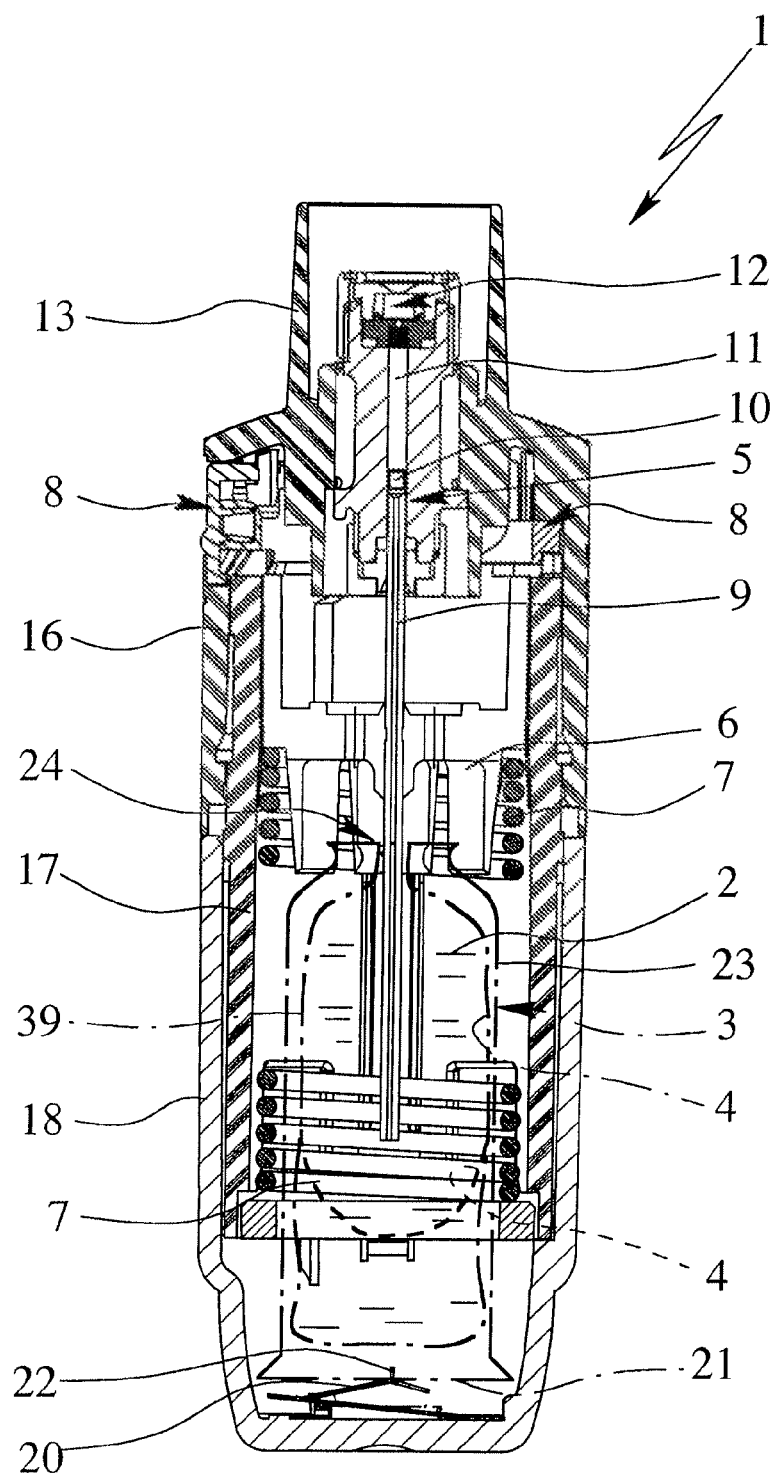

FIGS. 1 & 2 show a proposed nebulizer 1 for atomizing a fluid 2, particularly, a fluid or medicament preparation, in a schematic view in the relaxed state (FIG. 1) and in the tensioned state (FIG. 2). The nebulizer 1 is constructed, in particular, as a portable inhaler and/or preferably operates without propellant gas.

The atomization of the fluid 2 or medicament preparation preferably forms an aerosol 14 destined for the lungs (FIG. 1) which can be taken, particularly breathed in or inhaled, by a user or patient (not shown). Usually, the preparation is inhaled at least once a day, more particularly several times a day, preferably at set intervals, especially depending on the patient's complaint.

The nebulizer 1 has a preferably insertable, and optionally, replaceable reservoir 3 containing the fluid 2, as shown in FIGS. 1 and 2. Preferably, the reservoir 3 contains a sufficient quantity (typically 2 to 10 or 2 to 15 ml) of fluid 2 or active substance for a number of doses, e.g., 100 or more doses, to allow numerous atomizations or applications.

The reservoir 3 is preferably substantially cylindrical or cartridge-shaped and/or constructed as an in particular rigid container and/or may be inserted in the nebulizer 1 from below, for example, after the nebulizer has been opened, and may optionally be replaceable.

The reservoir 3 has a fluid chamber 4 containing the fluid 2, which is preferably constructed as a bag 39 or is formed thereby. The fluid chamber 4 or a wall bounding the fluid chamber 4 (in this case the bag wall) is preferably flexible, deformable and/or collapsible in construction, at least in parts.

The nebulizer 1 preferably has a conveying device, particularly a pressure generator 5, for conveying and/or atomizing the fluid 2, part in a predetermined, optionally adjustable metering quantity.

The nebulizer 1 or pressure generator 5 comprises, in particular, a holder 6 for the reservoir 3, an associated drive spring 7, shown only partially, preferably, with an associated locking element 8 that is manually operable for unlocking, a conveying element or conveying tube 9 preferably in the form of a capillary, an optional valve, particularly a non-return valve 10, a pressure chamber 11 and/or an expulsion nozzle 12, particularly in the region of a mouthpiece 13 or other end piece.

The reservoir 3 is fixed in the nebulizer 1 by means of the holder 6, particularly by a clamping or latching action, such that the conveying element extends into the fluid chamber 4 and/or is fluidically connected thereto. The holder 6 may be constructed so that the reservoir 3 is replaceable.

When the drive spring 7 is axially tensioned, the holder 6 with the reservoir 3 and the conveying element is moved downwards in the drawings and the fluid 2—more precisely the next dose—is sucked out of the reservoir 3 through the non-return valve 10 into the pressure chamber 11 of the pressure generator 5. The fluid chamber 4 (bag) collapses as a function of the removal of fluid 2.

During the subsequent relaxation of the drive spring 7, after actuation of the locking element 8 for atomization, the fluid 2 in the pressure chamber 11 is put under pressure by the conveying element being moved upwards, preferably solely by the force of the drive spring 7, with the non-return valve 10 now closed, the conveying element acting as a pressure ram. This pressure expels the fluid 2 through the expulsion nozzle 12, whereby it is atomized into the aerosol 14 preferably destined for the lungs as shown in FIG. 1.

The user or patient (not shown) can inhale the aerosol 14, while supply air can preferably be taken into the mouthpiece 13 through at least one supply air opening 15.

During the atomization process or stroke, the reservoir 3 is moved back into its original position by the drive spring 7. The reservoir 3 thus preferably performs a lifting movement during the tensioning process and during the atomization process.

Instead of the pressure generator 5 and/or drive spring 7 it is also possible to use other means and/or devices.

The nebulizer 1 comprises in particular a first housing part (upper part) 16 and an inner part 17 which is rotatable relative thereto (FIG. 2) having an upper part 17a and a lower part 17b (FIG. 1), while a manually operable or rotatable second housing part (lower part) 18 is releasably attached to, in particular pushed onto, the inner part 17, preferably by means of a safety lock or holding element 19. In particular, the safety lock or holding element 19 is designed such that there is no possibility of accidentally opening the nebulizer 1 or pulling off the second housing part 18. In particular, in order to release the second housing part 18, the holding element 19 has to be pressed in counter to the force of a spring. For inserting and/or changing the reservoir 3, the second housing part 18 can be detached from the atomizer 1. The second housing part 18 preferably forms a cap-like lower housing part and/or fits around or over a lower free end portion of the reservoir 3.

The second housing part 18 can be rotated relative to the first housing part 16, carrying the inner part 17 with it. As a result, the drive spring 7 is tensioned in the axial direction by a gear (not shown in detail) acting on the holder 6. As tensioning occurs, the reservoir 3 is moved axially downwards or with its end portion (further) into the second housing part 18 or towards the end face thereof until the reservoir 3 assumes an end position shown in FIG. 2. In this position, the drive spring 7 is tensioned.

The nebulizer 1, preferably, has means for forcibly venting the reservoir 3, particularly an optional outer casing 23 of the reservoir 3.

During tensioning for the first time, the outer casing 23 is, as required or optionally, pierced or opened at its base. In particular, an axially acting spring 20 arranged in the housing part 18 comes to abut on the base 21, this spring using a piercing element 22 to pierce the outer casing 23 or a bottom seal, particularly a gastight one, for ventilation when it comes to abut for the first time.

The forced ventilation device is thus produced, in this case, by the piercing element 22 which is held or formed by the spring 20. However, other design solutions are also possible.

It is noted that during the piercing for venting purposes only the outer casing 23 of the reservoir 3 is opened. The fluid chamber 4 (bag) containing the fluid 2 remains undamaged.

As the fluid 2 is removed through the conveying element, the flexible or deformable bag or fluid chamber 4 collapses. For pressure equalization, ambient air can flow into the reservoir 3 or outer casing 23 through the venting or piercing opening.

The means for forced venting are provided purely optionally. In particular, the means for forced venting may be omitted altogether, for example if the outer casing 23 of the reservoir 3 is already substantially gastight in construction and/or if other venting means, such as a valve, are provided.

In order to use the nebulizer 1, first of all, the reservoir 3 must be inserted. This is preferably done by removing or pulling off the second housing part 18. Then, the reservoir 3 is inserted or pushed axially into the inner part 17. It is then opened or attached at the head end. This is done by the conveying element, i.e., the conveying tube 9, which pierces a seal of the reservoir 3 preferably provided in particular at the end or head, and/or is subsequently inserted through a closure 24 provided in particular at the head end, preferably with a septum, into the interior of the reservoir 3 or fluid chamber 4. In this way, the fluidic connection is formed between the reservoir 3—or more precisely, between the fluid chamber 4 in the reservoir 3—via the conveying tube 9, with the pressure generator 5 or with the pressure chamber 11.

Then, the second housing part 18 is replaced or pushed back on. The nebulizer 1 can then be tensioned for the first time. Preferably, the reservoir 3 is then pierced, i.e., forcibly vented, at its base by the piercing element 22, as explained previously.

Before being used for the first time, after the reservoir 3 has been inserted or fluidically connected, the nebulizer 1 is preferably tensioned and actuated several times. This so-called priming causes any air present in the conveying element and/or in the pressure generator 5 as far as the expulsion nozzle 12 to be forced out of the fluid 2. The nebulizer 1 is then ready for delivery or inhalation.

The fluid chamber 4 or the wall thereof is constructed to be at least substantially or partially deformable, compressible and/or collapsible, as already mentioned. The fluid chamber 4 is preferably at least substantially or partially formed or made from or bounded by a flexible, deformable and/or collapsible material.

The fluid chamber 4 or the wall thereof is preferably substantially or partially or exclusively formed by the bag 39 or a tube or the like or is constructed as such.

Preferably, the flexible wall material used for the fluid chamber 4 is an in particular multilayered film or the like. However, even with multilayered films containing a metal layer, particularly an aluminum layer or foil, it has not hitherto been possible to achieve a fully gastight seal. As a result, gases are able to diffuse through the foil or wall of the fluid chamber 4.

If an ethanolic fluid 2 is used, for example, a partial air pressure which is substantially lower than the ambient pressure usually prevails in the fluid chamber 4. This partial pressure difference makes it possible for air to diffuse slowly into the fluid chamber through the film of wall of the fluid chamber 4. The resulting concentration of air in the fluid chamber 4 may lead to an unwanted increase in the pressure in the fluid chamber 4 and hence in the pressure acting on the fluid 2.

In the prior art, attempts have previously been made to fill the fluid chamber 4 as completely as possible with fluid 2. However, in practice, this could not be done totally without residual gas or gas bubbles. Usually, there is a small but nevertheless present residual gas bubble in the fluid chamber 4 after filling with the fluid 2. If an ethanolic fluid 2 is used, for example, the relatively low boiling point of ethanol and hence the vapor pressure of the ethanol, which varies considerably depending on the temperature, may lead to unwanted variations, particularly an unwanted increase, in the pressure in the fluid chamber 4 and hence the pressure acting on the fluid 2.

When the reservoir 3 or fluid chamber 4 is opened for the first time (in the embodiment shown, by inserting the reservoir 3 in the nebulizer 1 or by piercing the reservoir 3/fluid chamber 4) and an increased or high pressure prevails in the fluid chamber 4, the fluid 2 may possibly escape directly—i.e., without previous actuation of the nebulizer 1—through the expulsion nozzle 12, for example. This is undesirable.

Moreover, the insertion of the conveying element into the fluid chamber 4 may lead to an undesirable increase in pressure, particularly when the fluid chamber 4 is full to bursting.

According to a first aspect of the present invention, in order to avoid or minimize an undesirable pressure rise in the fluid chamber 4, it is envisaged that the fluid chamber 4 should be deformed, folded, creased, rolled, at least partly compressed and/or pre-collapsed when filled with the fluid 2 (this state, before and/or during the filling with fluid 2 is schematically indicated by the dotted line of the fluid chamber 4 in FIG. 2) and/or the maximum volume of the fluid chamber 4 is greater than the (initial) fill quantity with the fluid 2. This quasi incomplete filling is generally also referred to as "under-filling" for short.

The effect of the under-filling is that the air that diffuses into the fluid chamber 4 during storage of the sealed reservoir 3 or fluid chamber 4 (typically air diffusion rates into the fluid chamber 4 are about 2.5 microliter per day at 40° C. and 0.35 microliter per day at 20° C.) even after lengthy storage, does not lead to any (noticeable) increase in the pressure acting on the fluid 2 in the fluid chamber 4.

Accordingly, other potential pressure variations in the fluid chamber 4 occurring, for example, as a result of the evaporation of solvent from the fluid 2 are compensated for or prevented by the under-filling or further expandability of the fluid chamber 4.

In particular, the fluid chamber 4 can be increased in size and/or expanded beyond the initial fill quantity of fluid 2. Thus, volume increases in the fluid chamber (caused, for example, by the diffusion of air into the fluid chamber 4 and/or by the evaporation or volatilization or components of the fluid 2) can be compensated.

Particularly preferably, the maximum or initial fill quantity (in the case of partial filling with gas or, if there is residual gas in the fluid chamber 4, the total fill amount usually obtained initially at normal pressure) is less than 95%, preferably less than 90%, more particularly approximately 85% or less of the maximum volume of the fluid chamber 4.

The total volume or maximum volume of the fluid chamber 4 is preferably about 2 to 10 ml or 2 to 15 ml. More particularly, approximately 3 to 5 ml. However, other volumes are also possible.

The difference between the maximum volume of the fluid chamber 4 and the maximum or initial fill quantity of fluid 2 is preferably about 0.2 to 1.0 ml, more particularly, about 0.4 to 0.8 ml.

Experiments and simulations have shown that the proposal allows the still sealed reservoir 3 or fluid chamber 4 to be stored for very long periods (in particular, for more than 2 to 3 years) with a non-measurable or negligible increase in pressure in the fluid chamber 4, even under unfavorable conditions (for example, high temperatures and/or high rates of air diffusion into the fluid chamber 4).

Particularly preferably, the fluid chamber 4 is filled at least substantially so as to be free from residual gas or gas bubbles. Any gas bubble in the fluid chamber 4, which is often unavoidable during filling, is thus preferably kept as small as possible. In this case, instead of considering just the volume of fluid 2, the volume of the gas bubble at normal pressure can additionally be taken into account when determining the initial fill quantity.

According to an alternative embodiment described more fully hereinafter, filling which is at least substantially totally free from residual gas or gas bubbles is achieved, in particular.

According to a second aspect of the present invention which can also be achieved independently, the preferably flexible fluid chamber 4 is preferably filled with the fluid 2 under reduced pressure. This also helps to prevent or minimize an undesirable rise in the pressure in the fluid chamber 4, as the inclusion and/or formation of a gas bubble 28 in the fluid chamber 4 can be avoided or minimized. Filling under reduced pressure is carried out in particular in conjunction with the under-filling mentioned previously.

As already mentioned, the reservoir 3 preferably has an optional outer casing 23. In contrast to earlier designs, however, there is preferably no rigid, airtight shell surrounding the flexible deformable or collapsible fluid chamber 4, in particular, the bag or the like that forms the fluid chamber 4.

If the outer casing 23 is used in rigid form, it is preferably not sealed hermetically or in gastight manner, or it is preferably opened before the fluidic opening or attachment of the fluid chamber 4, for example, by piercing at its base, as described above or in some other suitable manner (for example, when the reservoir 3 is removed from packaging or the like (not shown here)).

Alternatively, the outer casing 23 itself may, in turn, be of flexible, deformable and/or collapsible design, particularly like the fluid chamber 4. In this case, the outer casing 23 in turn may be hermetically sealed or airtight in construction and/or may be connected to the wall that forms the fluid chamber 4 in part or over its entire surface, or may even be formed as a composite therewith.

As already mentioned, the fluid chamber 4 in the embodiment shown is preferably formed by a bag or a bag-like wall or the like. However, other design solutions are also possible.

The reservoir 3 can preferably be of sterile or sterilizable construction. Particularly preferably, the sealed reservoir 3 is of correspondingly temperature-resistant construction. Moreover, the closure 24 preferably seals the reservoir 3 in sterile manner.

It is noted that, generally, in the proposed nebulizer 1, the reservoir 3 can preferably be inserted, i.e., installed in the nebulizer 1. Consequently, the reservoir 3 is preferably a separate component. However, the reservoir 3 may theoretically also be formed directly by the nebulizer 1 or a part of the nebulizer 1 or otherwise integrated in the nebulizer 1.

In contrast to freestanding apparatus or the like, the proposed nebulizer 1 is preferably of a portable design and in particular is a portable hand-held device.

Particularly preferably, the nebulizer 1 is constructed as an inhaler, particularly for medical aerosol therapy. Alternatively, however, the nebulizer 1 may also be designed for other purposes.

Some additional embodiments and aspects of the present invention, which can also be realized independently, will be described in more detail hereinafter; in principle, only the differences or additional aspects will be discussed. The embodiments, explanations, features and advantages described hereinbefore still apply correspondingly or in a supplementary capacity.

Figure 3:
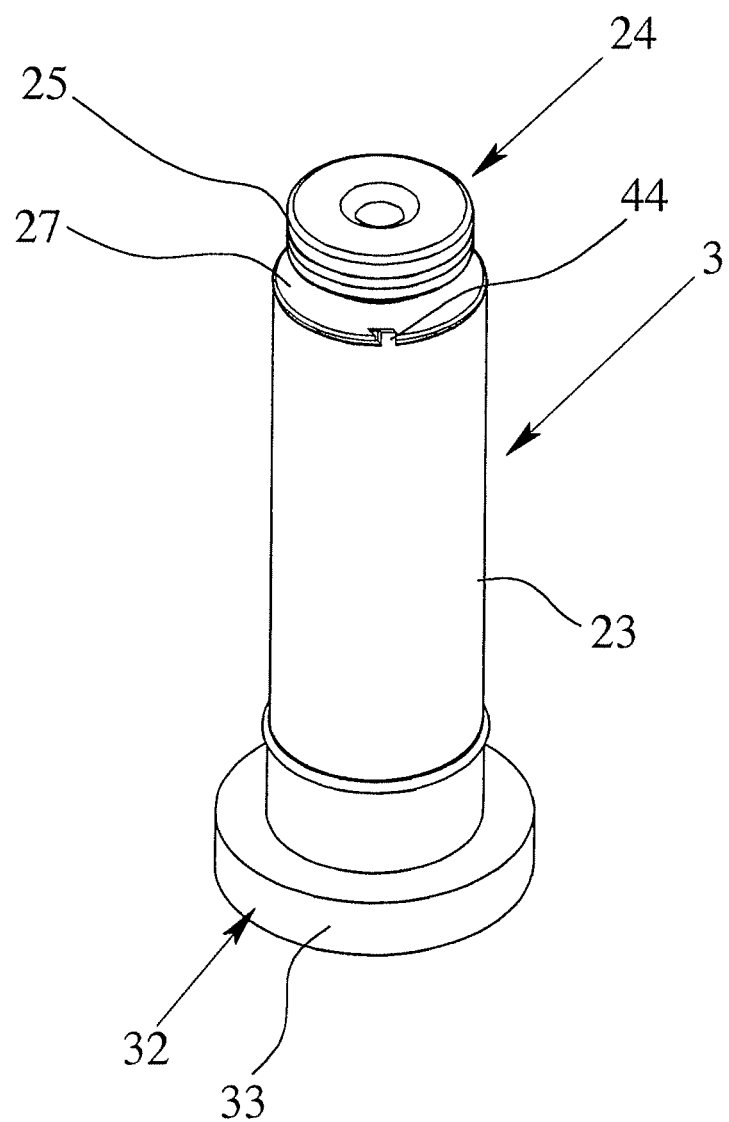
Figure 4:
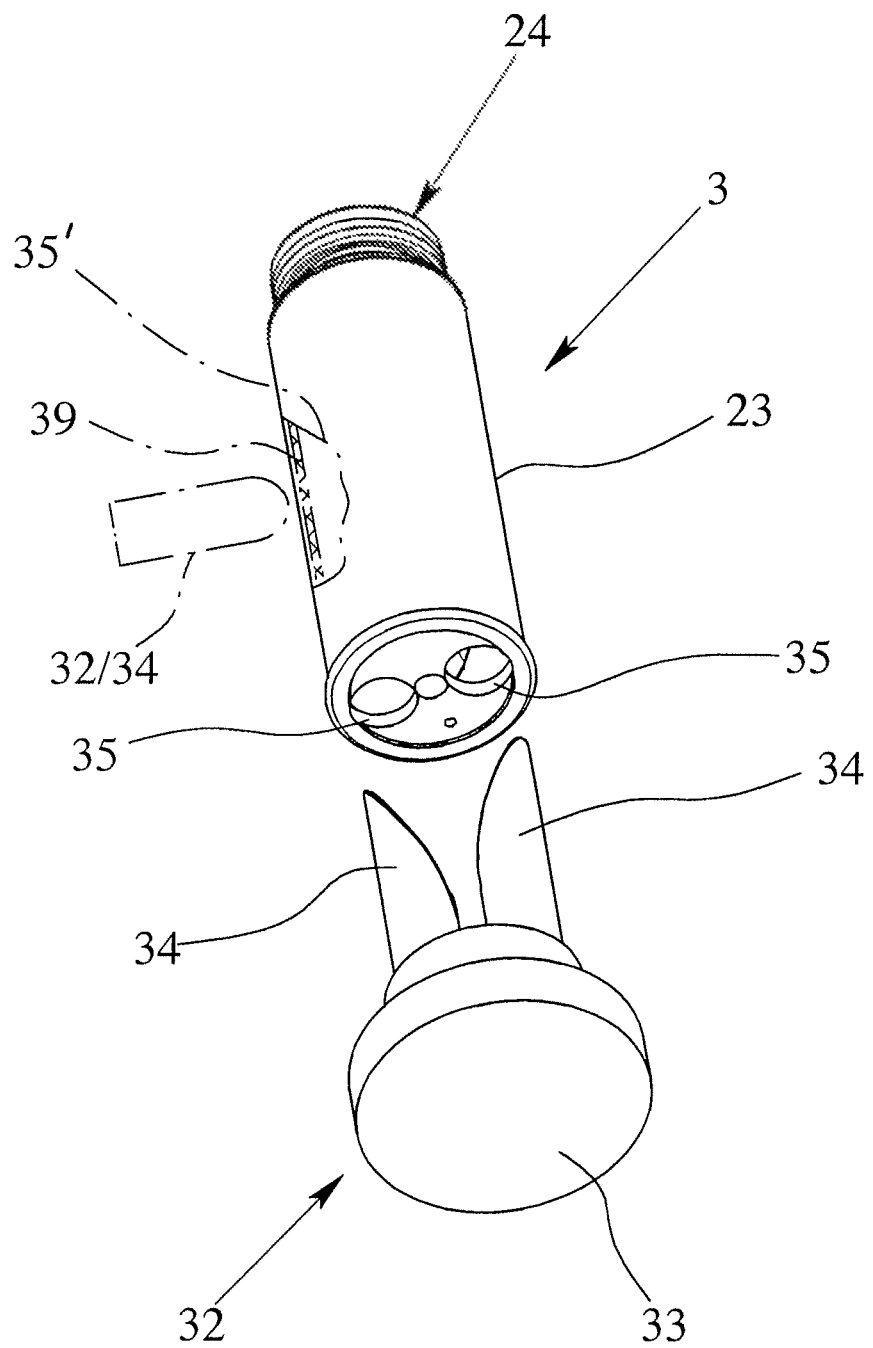
Figure 5:
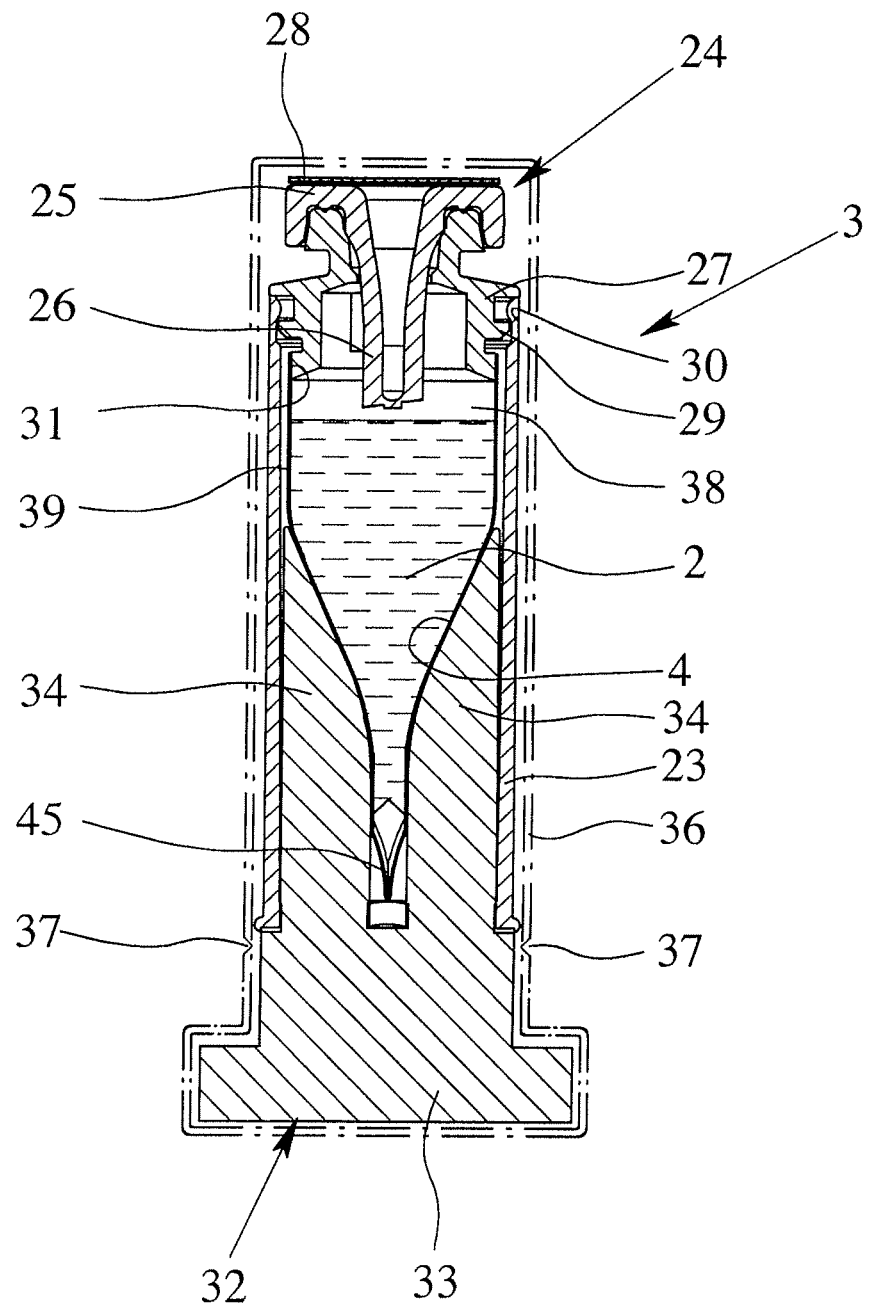

FIGS. 3 to 5 show a second embodiment of the proposed reservoir 3 in the uninstalled state, i.e., without the nebulizer 1 in which the reservoir 3 can be used. FIG. 3 shows the reservoir 3 in a perspective view, together with a device 32 for pre-collapsing the fluid chamber 4. FIG. 4 shows in a similar perspective view of the reservoir 3 with the device 32 detached or removed. FIG. 5 shows the reservoir 3 in schematic section in the packaged state. To begin with, FIG. 5 will be discussed in detail.

The reservoir 3 according to the second embodiment, as in the first embodiment, preferably has a closure 24. The latter preferably has a first closure member 25 which comprises or forms, in particular, an adjoining septum 26 for the insertable conveying element or conveying tube 9. However, the septum 26 may also be formed by another component. Furthermore, the septum 26 is only optional, i.e., it does not have to be provided.

In the embodiment shown, the closure 24 preferably has a second closure member 27. The second closure member 27 is connected to the first closure member 25 in gastight manner, particularly by welding. However, other design solutions are also possible. If necessary, the two closure members 25, 27 may also be formed by a single common component.

The closure 24 or the reservoir 3 preferably has a seal 28 which is preferably formed by a heat-sealing film or the like and serves to provide a hermetic or substantially gastight closure, so as to prevent or at least minimize the diffusion of air, in particular, through the first closure member 25 or the septum 26 thereof into the fluid chamber 4.

The closure 24 is preferably connected to the outer casing 23 or carried by it. In the embodiment shown, the closure 24 or the second closure member 27 preferably comprises, for this purpose, in particular, an annular or cylindrical connecting portion 29 for connecting to the outer casing 23.

The outer casing 23 can be connected to the closure 24 or connecting portion 29 by a clamping or latching action, in particular. In the embodiment shown, a projection or bead, particularly an annular bead 30, on the inside of the outer casing 23, may engage behind the connecting portion 29, so as to allow a sufficiently firm and/or interlockingly engaging connection between the outer casing 23 and the closure 24 by pushing together accordingly in the axial direction. However, other design solutions are also possible. Alternatively or additionally, the components may also be welded or glued to one another and/or attached by any other suitable means.

The closure 24, particularly the second closure part 27 thereof, is connected to the wall that forms the fluid chamber 4 or to the bag 39 or the like that forms or delimits the fluid chamber 4, in fluid-tight, and in particular, gastight manner, especially via a connecting region 31. Particularly preferably, the closure 24 or the second closure member 27 or connecting region 31 thereof carries the fluid chamber 4 or its wall. However, other design solutions are also possible.

In the embodiment shown, the wall or the bag 39 that forms the fluid chamber 4 is preferably welded and/or glued to the closure 24 or connecting region 31. However, other design solutions are also possible.

The wall of the fluid chamber 4 is preferably made from a material that is flexible and/or preferably easily deformable (elastically and/or inelastically) or deformable substantially without the application of force. A sheet material and/or composite film structure is particularly preferably used for this purpose. The wall material is hereinafter referred to as "film" for short.

As previously mentioned, the film is substantially impervious, particularly airtight, so that there is no need for an additional hermetic seal using a preferably metallic outer casing 23, as has previously been customary. Rather, the outer casing 23, in the embodiment shown, may be made, in particular, from plastics or the like and/or may be of open construction, as already mentioned and explained more fully hereinafter.

The film is preferably multilayered in construction and/or preferably contains a metal layer, particularly an aluminum layer or the like. Particularly preferably, the metal layer is covered by a layer of lacquer and/or plastics, preferably on the inside at least. Particularly preferably, the inner layer of the film consists of a material such as polyethylene, which can be directly attached, preferably by welding, to the closure 24 or to the inner or second closure member 27.

However, the film is often not completely impervious to gas, with the result that the possible diffusion of air into the fluid chamber 4 as mentioned above must be taken into consideration precisely when the still sealed reservoir 3 or fluid chamber 4 is stored for long periods.

Preferably, the fluid chamber 4 is pre-collapsed, before or during the filling with the fluid 2, to a volume which is less than the maximum volume of the fluid chamber 4. Thus the under-filling with fluid 2 mentioned previously can be achieved very easily.

Particularly preferably, the pre-collapsing, i.e., the reduction or restriction of the fill volume of the fluid chamber 4 from the level that is actually possible to a volume which is less than the maximum volume of the fluid chamber 4, takes place before and during the filling with fluid 2. However, it is theoretically also possible for the collapsing of the fluid chamber 4 to take place only when it is being filled with the fluid 2 or even after it has been filled with the fluid 2, for example by the application of reduced pressure and/or by other suitable methods such as compression or the like.

Particularly preferably, the fluid chamber 4 is externally put under pressure and/or externally limited in its spatial expansion before or during the filling with the fluid 2. This is a very simple method of achieving the desired pre-collapsing and/or under-filling.

For the pre-collapsing, a gaseous, liquid and/or solid medium or agent may act on the fluid chamber 4 or the wall thereof—the film, in the embodiment shown—from outside, particularly in order to reduce the size of the fluid chamber 4 compared with its maximum volume.

It is also possible to expand the bag 39, tube or the like that forms the fluid chamber 4 less than completely, or to keep it still creased, rolled or folded or compressed, before or during the filling with the fluid 2.

The preferred pre-collapsing is carried out in particular mechanically, as explained hereinafter by reference to the embodiment shown.

In the second embodiment, the device 32 is preferably used to pre-collapse the fluid chamber 4. The device 32 optionally has a handle 33 or holder in the embodiment shown and preferably has at least one manipulating or abutment element 34, particularly preferably two abutment elements 34, as shown in FIGS. 3 to 5. The description that follows refers in every case to two abutment elements 34 or a plurality of abutment elements 34. However, only one abutment element 34 or other manipulating element or the like may be provided. The following remarks apply accordingly.

The abutment elements 34 are preferably elongate, rod-shaped and/or pin-shaped in the embodiment shown, but may optionally also be in the form of tongs or cheeks.

The abutment elements 34 are preferably of rigid construction in the embodiment shown but may also be of flexible or elastically deformable construction. For example, the abutment elements 34—individually or together—may also be held, biased or formed by a spring.

The abutment elements 34 preferably have rounded or rounded-off abutment surfaces and/or edges for abutting on the wall of the fluid chamber 4. In particular the free ends of the abutment elements 34 are rounded off.

The abutment elements 34 are preferably formed on the handle 33 or other holder or formed thereby.

The device 32 or its abutment elements 34 are preferably adapted to the reservoir 3 or its outer casing 23 such that it is possible to engage between the wall of the fluid chamber 4 or the bag 39, on the one hand, and the outer casing 23, on the other hand, and/or the fluid chamber 4 can be compressed or pre-collapsed axially and/or radially and/or on opposite sides.

By means of the abutment elements 34, the fluid chamber 4, or more precisely the wall that forms the fluid chamber 4 or the bag 39, tube or the like that forms the fluid chamber 4—is deformed, pressed in, at least partially compressed and/or pre-collapsed. In the embodiment shown, this is achieved, in particular, by placing the device 32 or the abutment elements 34 on the reservoir 3 or its outer casing 23 or pushing it or them into it, as shown in FIGS. 3 & 5. However, the abutment elements 34 may also act on the outside of the wall of the fluid chamber 4 independently of the outer casing 23. For example, in the course of the manufacturing process, before the assembly of the reservoir 3 or connection to the outer casing 23, the desired pre-collapsing may be carried out by the action of abutment elements 34 or by another method during the filling with fluid 2.

As a result of the external placement of the abutment elements 34 against the wall of the fluid chamber 4 or the deformation thereof, the actual volume of the fluid chamber 4 available during the filling with the fluid 2 is reduced, i.e., it is less than the maximum volume of the fluid chamber 4. This results in the desired pre-collapsing.

It should be noted that the deformation or pre-collapsing of the fluid chamber 4, particularly by the external placement of at least one abutment element 34, or a temporary restriction in the expansion of the fluid chamber 4 thus produced takes place, particularly preferably, during the filling of the fluid chamber 4 with the fluid 2. However, according to an alternative embodiment this may take place only before the fluid chamber 4 is filled with the fluid 2, i.e., the at least one abutment element 34 has to be removed or withdrawn before the filling operation. This is achieved or made possible, in particular, by the fact that the filing of the fluid chamber 4 with the fluid 2 takes place at very low pressure or even substantially without pressure and/or the wall of the fluid chamber 4 or the bag 39, tube or the like does not expand again when filled with the fluid 2, even without any external restriction, particularly because the forces produced during the filling with the fluid 2 are not sufficient for this purpose. This also applies accordingly if the pre-collapsing is carried out not by the mechanical placement of at least one abutment element 34 but by some other method.

The fluid chamber 4 is preferably placed under pressure externally and/or externally restricted in its spatial expansion, before or during the filling with the fluid 2, by means of the abutment elements 34 in the embodiment shown. However, it is also theoretically also possible to provide internal or other restrictions. For example, the fluid chamber 4 or the walls thereof may also be deformed, folded, creased, rolled, pressed in and/or at least partially compressed in some other way. This method of pre-collapsing may be carried out in addition to or instead of the external abutment or effect of the abutment elements 34.

In particular, pre-collapsing is carried out to less than 95%, preferably less than 90%, more especially about 85% or less of the maximum volume of the fluid chamber 4. Thus, the fluid chamber 4 is preferably pre-collapsed to a volume which is less than its maximum volume before or during the filling with the fluid 2.

As a result of the pre-collapsing of the fluid chamber 4 the (initial) fill quantity of fluid 2 is preferably forcibly restricted so as to achieve the desired under-filling.

In the embodiment shown, the reservoir 3 or its outer casing 23 preferably has at least one opening 35, in this case two axial openings 35, to accommodate the abutment elements 34, as shown in FIG. 4. However, other design solutions are also possible.

According to an alternative embodiment indicated by dotted lines in FIG. 4, pre-collapsing of the fluid chamber 4 may be carried out alternatively or additionally by having at least one abutment element 34 engage, for example, laterally or radially on the wall of the fluid chamber 4 or on the bag 39 and/or engaging or acting laterally or radially upon the reservoir 3 or its outer casing 23, for example, through the lateral opening 35', such as a slot, shown only by dotted lines or opposing lateral openings 35'.

According to an alternative embodiment not shown here, the reservoir 3 or the outer casing 23 may also form or comprise an outer wall which is openable or deformable at least in parts, which is deformable or compressible, in particular, by means of the device 32 or at least one abutment element 32 for pre-collapsing the fluid chamber 4, particularly inwardly. Alternatively, the reservoir 3 or the outer casing 23 may also be variable or adjustable in length or some other dimension, for example, telescopically or in a concertina fashion, for pre-collapsing the fluid chamber 4.

For example, the abutment element 34 may also be designed to be clipped shut, clamped and/or self-maintaining.

The schematic section in FIG. 5 shows the pre-collapsed fluid chamber 4 which has already been filled with fluid 2 under the effect of the device 32 or abutment elements 34. After the detachment or removal of the device 32 or the abutment elements 34, the fluid chamber 4 can be enlarged again or expand (optionally even to its maximum volume which is greater), particularly, by the diffusion of air or certain gases into it, the evaporation of components of the fluid 2 in the fluid chamber 4, the expansion of a gas bubble 38 contained therein and/or other effects.

After the filling of the fluid chamber 4 the device 32 or the placement of the abutment elements 34 can be immediately removed or reversed. However, it is also possible for this to take place only when the reservoir 3 is removed from its packaging and/or when the reservoir 3 is placed in the nebulizer 1.

The fluid chamber 4 or bag 39 is closed off at its end 45 remote from the closure 24 by means of a flat seam, in particular, preferably a weld seam or by some other, particularly flat end portion, as schematically shown in FIG. 5. The fluid chamber 4 or its outer wall or the bag 39, tube or the like is thus preferably constructed to be non-rotationally symmetrical or non-circular, at least partially, in the region of the end 45, but has a different or flat cross-section at this point. The abutment elements 34 preferably engage on the wall of the fluid chamber 4 or on the bag 39 in the region of this divergent or flat cross-sectional shape or outer contour. In the embodiment shown, the abutment elements 34 preferably act on opposite sides of the flat end portion, particularly so that the flat weld seam runs between them or is accommodated between them. However, different orientations are also possible.

According to a preferred aspect of the present invention, particularly in order to achieve the abovementioned or a desired orientation of the abutment elements 34 relative to the fluid chamber 4 or bag 39 or the like, the closure 24 with the fluid chamber 4 or bag 39 preferably has a defined rotational position relative to the outer casing 23 or to the at least one opening 35. This defined rotational position is preferably achieved in the embodiment shown by a defined engagement or protection against rotation, particularly between the outer casing 23 and the closure 24, which is schematically shown in FIG. 3. In the embodiment shown, the closure 24 or the second closure part 27 thereof, on the one hand, and the outer casing 23, on the other hand, preferably, engage axially and/or radially in one another (for example, by means of corresponding teeth, latching, a tongue-like projection or the like) so as to secure a defined rotational position. However, other design solutions are also possible.

In the embodiment shown, the filled and closed reservoir 3 is accommodated, together with the device 32, for example, in joint packaging 36. The packaging 36 is preferably constructed so that when the package 36 is opened the device 32 is detached from the reservoir 3. This can be achieved, for example, if the packaging 36 has at least one frangible point 37 or the like and/or the packaging 36 can be primarily detached only from the reservoir 3 but not from the opening 32. However, other design solutions are also possible.

After the packaging 36 has been opened and the reservoir 3 removed from its packaging, and the reservoir 3 separated from the device 32, the reservoir 3 is inserted in the nebulizer 1, as described previously. In this state of the reservoir 3, the fluid chamber 4 is able to expand or enlarge beyond the initial fill volume with fluid 2, particularly, into the area that had been pressed in by the abutment elements 34 and has now been released, so that when the reservoir 3 or fluid chamber 4 is fluidically connected there, is no undesirable excess pressure in the fluid chamber 4, and therefore, an undesirable escape of fluid 2 or the like is prevented.

The proposed under-filling or expandability of the fluid chamber 4, alternatively or additionally, has the advantage that, when the conveying element or conveying tube 9 is inserted in the fluid chamber 4, again an undesirable rise in pressure in the fluid chamber 4, and hence, in particular, the premature outflow of fluid 2 through the conveying element or in some other manner can be avoided as, once again, there is no (meaningful) rise in pressure in the fluid chamber 4, since the fluid chamber 4 is able to expand.

It should be noted that the device 32 for pre-collapsing can be removed or detached or pulled away directly after the fluid chamber 4 has been filled with the fluid 2. In particular, the device 32 may be a device which is totally separate from the reservoir 3, for example, associated with a filling device or the like. In particular, the restriction to the spatial expansion and/or the action of external pressure on the fluid chamber 4 or on its walls can be stopped immediately after the filling with the fluid 2.

Particularly preferably, the fluid chamber 4 or its walls or the bag 39, tube or the like is expanded before the filling of the fluid chamber 4. The term "expansion" used hereinafter always refers to expansion before the filling with the fluid 2.

The expansion of the fluid chamber 4 may be carried out independently of the under-filling and/or pre-collapsing.

The expansion of the fluid chamber 4 is preferably carried out to a defined volume which is less than the maximum volume of the fluid chamber 4.

Preferably, the expansion takes place in conjunction with pre-collapsing. The expansion is used, in particular, to so to speak "inflate" the fluid chamber 4 to a volume defined by the pre-collapsing. Thus, in particular, a defined volume of the fluid chamber 4 can be achieved during the subsequent filling with the fluid 2.

The expansion of the fluid chamber 4 is preferably carried out using gas, hereinafter referred to as expansion gas. The expansion gas used is preferably an inert gas, carbon dioxide or helium or simply air.

The fluid chamber 4 may be filled with the fluid 2 under reduced pressure, according to an alternative embodiment. This filling under reduced pressure may also be carried out independently of the preferred pre-collapsing or under-filling. Preferably, however, the filling under reduced pressure takes place in conjunction with the pre-collapsing or under-filling. As a result of filling at reduced pressure, it is possible to achieve filling which is at least substantially free from residual gas or gas bubbles. The term "reduced pressure filling" encompasses the sealing of the filled fluid chamber 4 under reduced pressure, even if the filling itself has not taken place under reduced pressure.

Regardless of the filling at reduced pressure, the fluid volume 4 is preferably filled with the fluid 2 at least substantially without residual gas or gas bubbles. However, filling with a gas or a gas bubble 38, as schematically shown in FIG. 5, is also theoretically possible. This filling with the deliberate formation of a gas bubble 38 can generally also be used independently of the pre-collapsing and/or under-filling.

According to a preferred alternative embodiment of the process, it is not air that is used, but a component, another composition or a different gas that is used to form the gas bubble 38, particularly, a gas that can diffuse outwards relatively easily through the wall of the fluid chamber 4 and/or through the closure 24 and/or can be absorbed relatively easily by the fluid 2. Such gases include, in particular, pure oxygen, carbon dioxide, helium, (other) inert or protective gases and/or mixtures possibly with other gases.

The gas for forming the gas bubble 38 can be introduced by suitable flushing, after the fluid chamber 4 has been filled with the fluid 2. Alternatively or additionally, the filling of the fluid chamber 4 with the fluid 2 may also take place directly under the desired gas atmosphere. Alternatively or additionally, the gas, particularly carbon dioxide, may initially be at least partly or completely dissolved in the fluid 2 on entering the fluid chamber 4, so as to form the gas bubble 38 at that stage.

According to an alternative embodiment of the process, the desired gas for forming the gas bubble 38 may be used directly as the expansion gas for the previous expansion of the fluid chamber 4.

In the embodiment shown the fluid chamber 4 or its wall is preferably formed by the bag 39, as shown in FIG. 5. However, other design solutions are also possible in order to achieve the preferred flexibility, deformability and/or collapsibility.

According to an additional or alternative embodiment the fluid chamber 4 may also initially be filled completely or to the maximum level with the fluid 2. As a result the abovementioned expansion of the fluid chamber 4 to its maximum volume can take place, for example, so that there is no need for a separate expansion step, e.g., filling with gas beforehand. Then, some of the fluid 2 is removed from the fluid chamber 4 again, for example, by suction and/or externally collapsing the fluid chamber 4 in order to achieve the desired pre-collapsing and/or under-filling of the fluid chamber 4 during the subsequent closure of the fluid chamber 4.

According to another alternative embodiment which can be implemented additionally or alternatively, the fluid 2 is poured into the fluid chamber 4 at elevated temperature, and optionally, also under increased pressure. The fluid chamber 4 is then preferably sealed while the fluid 2 is still warm or hot. During the subsequent cooling there is a reduction in volume, which makes it possible to achieve the desired pre-collapsing of the fluid chamber 4. If the filling is carried out under increased pressure, this will increase the boiling point for low boiling substances. Alternatively or additionally, this can be used to test the pressure resistance of the fluid chamber 4.

According to an alternative embodiment not shown here, the device 32 or at least one abutment element 34 may also be connected or connectable to the outer casing 23 (releasable or non-releasable) and/or may be formed thereby. In particular, it is then also possible to remove the outer casing 23 which is provided with or connected to the device 32 once the pre-collapsed fluid chamber 4 has been filled with the fluid 2, and/or to replace it with another outer casing 23 without a device 32 or abutment element 34.

According to an alternative embodiment not shown here, the outer casing 23—also in combination with other alternative embodiments—may be of multi-part construction, particularly in two parts, most preferably in the form of two particularly identical half-shells, so that the parts of the casing or shells may be assembled and/or dismantled radially and/or axially.

Generally speaking, the bag or fluid chamber 4 may also be pre-formed, folded, creased or rolled or inserted in the outer casing 23 such that the subsequent deformation by the device 32 or by other means such as gas, liquid or the like is assisted or made possible.

Figure 6:
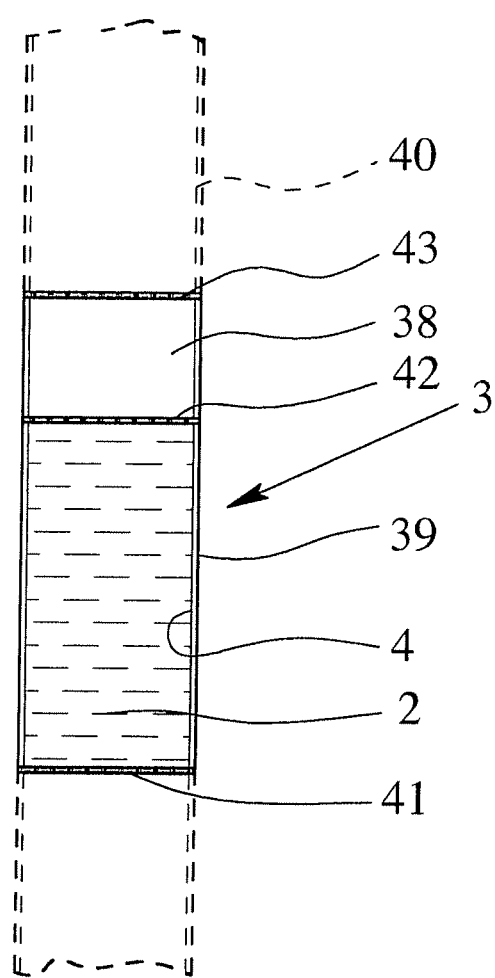

FIG. 6 shows a third embodiment of the proposed reservoir 3. The fluid chamber 4 is formed or made, in particular, from a tube 40, particularly an endless tube. This produces a tubular fluid chamber 4, in particular.

In the third embodiment, the fluid chamber 4 is preferably capable of being separated or has been separated by means of weld seams 41, 42, 43. Theoretically, by using the tube 40 to form the fluid chamber 4, filling with fluid 2 without any gas bubbles is made easier. For example, after filling, welding may be carried out such that no gas bubbles 38 remain in the fluid chamber 4 (e.g., welding of the bag in or with fluid 2). In particular, it is also possible initially to delimit the fluid chamber 4 by means of two external weld seams 41, 43 and then to separate off any gas bubble 38 still remaining by means of an additional weld seam 42 which is to be arranged between the other weld seams 41, 43, as shown in FIG. 6. However, other procedures are also possible.

Preferably several separate or separable fluid chambers 4 containing fluid 2 or reservoirs 3 are formed from the endless tube.

If the reservoir 3 or the fluid chamber 4 contains a gas bubble 38, as described as an optional variant in the second and third embodiments hereinbefore, it is sensible or necessary to measure the size of the gas bubble 38. This is preferably done using the measuring process described below, which can also be used independently.

The reservoir 3 or the deformable fluid chamber 4 containing the gas bubble 38 is placed in a sealed pressure chamber. The chamber is completely filled with an incompressible liquid. The incompressible liquid in the chamber is placed under pressure using a piston or other means. Depending on the pressure the gas bubble 38 and hence the flexible, compressible or collapsible fluid chamber 4 is also compressed. The incompressible liquid exhibits a corresponding change in volume. The change in volume can be determined by measuring the volume displaced by the piston, particularly, by measuring the displacement of the piston or by other means. The size of the gas bubble 38 can be determined by the pressure dependent change in volume, i.e., the pressure pattern.

The measuring process described above is well suited to determining the size of gas bubbles 38 in collapsible fluid chambers 4 and also for other purposes.

Individual features, aspects and/or principles of the embodiments and alternative features described may also be used independently of one another and combined with one another as desired and may be used not only in the nebulizer according to FIGS. 1 and 2 but also in other or similar nebulizers and inhalers.

In particular, the proposed reservoir 3 and the present invention may be used generally in the nebulizers or inhalers which are described in the publications listed below, or are based on their principles: U.S. patent application Publication Nos. 2002/0153006, 2003/0127538, 2003/0100964, 2005/0034723, 2004/0163646, 2005/0172957, 2005/0133029, 2005/0224076, 2005/0268911, U.S. Pat. No. 5,915,378, WO 03/041774, WO 2004/078244, Japanese Patent Application Publication Nos. JP 2004-283244, JP 2004-0283245, JP 2004-249208, JP 2005/058421 International Patent Application Publication Nos. WO 2004/022128, WO 2004/039442, and European Patent Application Nos. EP 1 236 517, EP 1 604 701, EP 1 561 484, EP 1 562 094.

Preferably, the fluid 2 is a liquid, as already mentioned, particularly an aqueous or ethanolic medicament formulation. However, it may also be a different medicament formulation, a suspension or the like, or particles or powders.

Some preferred ingredients, compounds and/or formulations of the preferably medical fluid 2 are listed below. As already mentioned, they may be aqueous or non-aqueous solutions, mixtures, ethanol-containing or solvent-free formulations or the like.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide
5-[2-(5,6-diethyl-indan-2-ylamino)-1-hydroxy-ethyl]-8-hydroxy-1H-quinolin-2-one
-4-hydroxy-7-[2-{[2-{[3-(2-phenylethoxy)propyl]sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1.1 dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide optionally, in the form of the racemates, enantiomers, diastereomers thereof and optionally in the form of the pharmacologically acceptable acid addition salts, solvates or hydrates thereof. According to the invention, the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

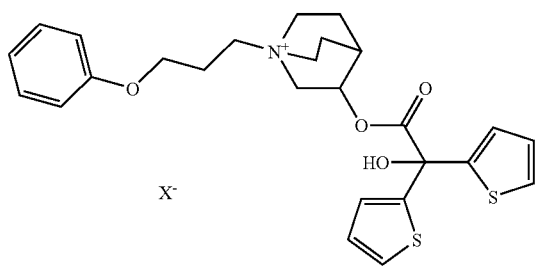

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

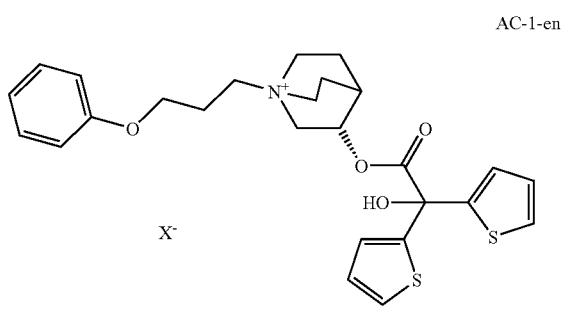

AC-1-en wherein X⁻ may have the above-mentioned meanings. Other preferred anticholinergics are selected from the salts of formula AC-2

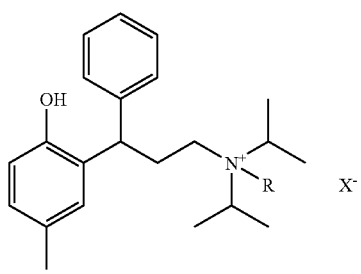

AC-2 wherein R denotes either methyl or ethyl and wherein X⁻ may have the above-mentioned meanings. In an alternative embodiment the compound of formula AC-2 may also be present in the form of the free base AC-2-base.

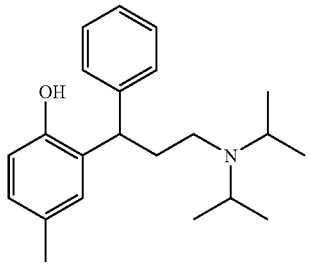

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the metho-X salts are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3 S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)$_p$-[(4aR*, 10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-5-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxyethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethy-lamino)-1-oxo-2-buten-1-yl]amino}-7-((R)-tetrahydrofu-ran-3-yloxy)-quinazoline 4-[(3-chloro-4-fluorophenyl)amino]-6-{[4-(N,N-dimethy-lamino)-1-oxo-2-buten-1-yl]amino}-7-((S)-tetrahydrofu-ran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclo-pentyloxy-quinazoline 4-[(3-chloro-4-fluorophenyl)amino]-6-{[4-(N,N-dimethy-lamino)-1-oxo-2-buten-1-yl]amino}-7-[(R)-(tetrahydro-furan-2-yl)methoxy]-quinazoline 4-[(3-chloro-4-fluorophenyl)amino]-6-{[4-(N,N-dimethy-lamino)-1-oxo-2-buten-1-yl]amino}-7-[(S)-(tetrahydro-furan-2-yl)methoxy]-quinazoline 4-[(3-ethynyl-phenyl)amino]-6,7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-mor-pholin-4-yl)-piperidin-1-yl]-ethoxy}-7-methoxy-quinazoline 4-[(3-chloro-4-fluoro-phenyl)amino]-6-[1-(tert.-butyloxy-carbonyl)-piperidin-4-yloxy]-7-methoxy-quinazoline 4-[(3-chloro-4-fluoro-phenyl)amino]-6-(trans-4-amino-cy-clohexan-1-yloxy)-7-methoxy-quinazoline 4-[(3-chloro-4-fluoro-phenyl)amino]-6-(trans-4-methane-sulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperi-din-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxym-ethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofu-ran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethy-lamino)sulphonylamino]-cyclohexan-1-yloxy}-7-meth-oxy-quinazoline 4-[(3-chloro-4-fluoro-phenyl)amino]-6-{trans-4-[(morpho-lin-4-yl)carbonylamino]-cyclohexan-1-yloxy}-7-meth-oxy-quinazoline 4-[(3-chloro-4-fluoro-phenyl)amino]-6-{trans-4-[(morpho-lin-4-yl)sulphonylamino]-cyclohexan-1-yloxy}-7-meth-oxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazo-line 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonyl-methyl-piperidin-4-yloxy)-7-methoxy-quinazoline 4-[(3-chloro-4-fluoro-phenyl)amino]-6-(cis-4-{N-[(tetrahy-dropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(mor-pholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(mor-pholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethane-sulphonylamino-cyclohexan-1-yloxy)-7-methoxy-quinazoline 4-[(3-chloro-4-fluoro-phenyl)amino]-6-(1-methanesulpho-nyl-piperidin-4-yloxy)-7-ethoxy-quinazoline 4-[(3-chloro-4-fluoro-phenyl)amino]-6-(1-methanesulpho-nyl-piperidin-4-yloxy)-7-(2-methoxy-ethoxy)-quinazo-line 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperi-din-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-me-thyl-piperazin-1-yl)carbonyl]-N-methyl-amino}-cyclo-hexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-$N^2$-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules as disclosed in EP 1 003 478 A1 or CA 2297174 A1 may also be used.

In addition, the compound may be selected from among the ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

What is claimed is:

1. Method of producing a reservoir for a nebulizer, comprising the steps of:
    partially filling a deformable fluid chamber with a fluid,
    disposing the deformable fluid-containing chamber within a reservoir housing, and
    compressing or pre-collapsing the fluid-containing chamber using at least one releasable or separable element that is inserted into the reservoir housing.

2. Method according to claim 1, wherein said releasable or separable element comprises at least one abutment element.

3. Method according to claim 2, comprising the further step of subsequently removing said at least one abutment element.

4. Method of producing a reservoir for a nebulizer, comprising the following steps of:
   partially filling a deformable fluid chamber with an initial quantity of a fluid,
   disposing the deformable fluid-containing chamber within a reservoir housing, and
   using at least one releasable or separable element for temporarily compressing or pre-collapsing the fluid chamber to a volume which is less than a maximum volume of the fluid-containing chamber before or while performing said filling step.

5. Method according to claim 4, with at least one of the following steps:
   filling the fluid chamber under a protective gas or vapor and forming a gas bubble of protective gas or vapor in the fluid chamber;
   sealing the fluid chamber free of gas bubbles;
   sealing the fluid chamber while the fluid therein is at an elevated temperature;
   initially completely filling the fluid chamber with fluid and then removing some fluid from the fluid chamber by suction before the fluid chamber is sealed;
   expanding the fluid chamber to a defined volume which is less than a maximum volume thereof before filling the chamber with the fluid;
   forming a gas bubble during filling of the fluid chamber from a gas which is at least partly dissolvable in the fluid.

6. Method according to claim 5, wherein the initial quantity of fluid is less than 95% of the maximum volume of the fluid chamber.

7. Method according to claim 4, wherein the initial quantity of fluid is less than 95% of the maximum volume of the fluid chamber.

8. Method according to claim 4, wherein said releasable or separable element comprises at least one abutment element.

9. Method according to claim 8, comprising the further step of subsequently removing said at least one abutment element.

10. Method of producing a reservoir for a nebulizer, comprising at least the following steps of:
    under-filling a deformable fluid chamber with an initial quantity of a fluid to a volume which is less than a maximum volume of the container;
    temporarily restricting the capacity of the deformable fluid chamber by deforming said deformable fluid chamber to said volume that is less than said maximum volume of the fluid-containing chamber at least one of before and during said under-filling step using at least one releasable or separable element to compress or pre-collapse the deformable fluid chamber; and
    sealing the fluid-containing chamber in an under-filled state for preventing a rise in the pressure in the fluid-containing chamber when the sealed reservoir is stored for long periods of time such that, when the chamber is opened for the first time by piercing, an escape or loss of the fluid due to pressure build is prevented.

11. Method of producing a reservoir for a nebulizer according to claim 10, wherein said restricting step is performed using a pair of abutment members which are moved against opposite sides of the fluid chamber as said releasable or separable element.

12. Method according to claim 10, wherein said releasable or separable element comprises at least one abutment element.

13. Method according to claim 12, comprising the further step of subsequently removing said at least one abutment element.

14. Method of producing a reservoir for a nebulizer, comprising the steps of:
    disposing a deformable chamber within a reservoir housing,
    compressing or pre-collapsing the deformable chamber using at least one releasable or separable element that is inserted into the reservoir housing, and
    partially filling the compressed or pre-collapsed deformable fluid chamber with a fluid.

15. Method according to claim 14, wherein the at least one releasable or separable element is withdrawn from the reservoir housing after the deformable fluid chamber has been compressed or pre-collapsed.

16. Method according to claim 14, wherein said compressing or pre-collapsing step comprises moving a pair of abutment members against opposite sides of the deformable fluid chamber as said at least one releasable or separable element.

17. Method according to claim 14, wherein the at least one releasable or separable element is withdrawn from the reservoir housing after said partial filling of the deformable fluid chamber.

18. Method according to claim 17, wherein the reservoir is closed or sealed after the at least one releasable or separable element has been withdrawn from the reservoir housing.

19. Method according to claim 14, wherein the deformable fluid chamber is closed or sealed after said partial filling.

20. Method according to claim 14, wherein the fluid with which the deformable fluid chamber partially filled is a medicament.

* * * * *